United States Patent [19]
Nissen

[11] Patent Number: 6,103,764
[45] Date of Patent: Aug. 15, 2000

[54] METHOD FOR INCREASING THE AEROBIC CAPACITY OF MUSCLE

[75] Inventor: Steven L. Nissen, Ames, Iowa

[73] Assignee: Iowa State University Research Foundation, Inc., Ames, Iowa

[21] Appl. No.: 09/187,265

[22] Filed: Nov. 6, 1998

Related U.S. Application Data

[60] Provisional application No. 60/064,948, Nov. 7, 1997.

[51] Int. Cl.⁷ .................................................. A61K 31/19
[52] U.S. Cl. ........................................... 514/557; 514/558
[58] Field of Search ..................................... 514/558, 557

[56] References Cited

U.S. PATENT DOCUMENTS

| | | |
|---|---|---|
| 4,992,470 | 2/1991 | Nissen . |
| 5,028,440 | 7/1991 | Nissen . |
| 5,348,979 | 9/1994 | Nissen et al. . |
| 5,360,613 | 11/1994 | Nissen . |
| 5,756,469 | 5/1998 | Beale . |

OTHER PUBLICATIONS

Miller et al., *FASEB J.*, 11(3), A 290 (1997).
Nissen et al., *J. Appl. Physiol.*, 81(5), 2095–2104 (1996).
Sandberg et al., *J. Anim. Sci.*, 75(Suppl. 1), 198 (1997).
Vukovich et al., *Med. & Sci. in Sports & Exercise*, 29, S 252 (1997).

*Primary Examiner*—Rebecca Cook
*Attorney, Agent, or Firm*—Leydig, Voit & Mayer, Ltd.

[57] ABSTRACT

The present invention provides a method for increasing the aerobic capacity of muscle of an animal, the method comprising administering a dose of HMB to the animal such that the aerobic capacity is increased without a substantial increase in the mass of the muscle. The present invention also provides a method for increasing the amount of hemoglobin in the blood of an animal having muscles, the method comprising administering a dose of HMB to the animal such that the amount of hemoglobin in the animal is increased without a substantial increase in the mass of the muscles.

17 Claims, No Drawings

METHOD FOR INCREASING THE AEROBIC CAPACITY OF MUSCLE

This application claims priority to provisional U.S. patent application Ser. No. 60/064,948, which was filed on Nov. 7, 1997.

TECHNICAL FIELD OF THE INVENTION

The present invention relates to a method for increasing the aerobic capacity of muscle and related methods.

BACKGROUND OF THE INVENTION

The only product of leucine metabolism is ketoisocaproate (KIC), and a minor product of KIC metabolism is β-hydroxy-β-methylbutyric acid (HMB).

HMB has been found to be useful within the context of a variety of applications. Specifically, as described in U.S. Pat. No. 5,360,613 (Nissen), HMB is useful for reducing blood levels of total cholesterol and low-density lipoprotein cholesterol. In U.S. Pat. No. 5,348,979 (Nissen et al.), HMB is described as being useful for promoting nitrogen retention in humans. U.S. Pat. No. 5,028,440 (Nissen) discusses the use of HMB to increase lean tissue development in meat-producing animals. Also, in U.S. Pat. No. 4,992,470 (Nissen), HMB is described as being effective in enhancing the immune response of mammals.

More recently, HMB has been used by athletes to increase strength. As described in Nissen et al., *J. Appl. Physiol.*, 81(5): 2095–2104 (1996), the increase in the strength of the athlete is the result of an increase in muscle mass which occurs when weight, or resistance, training is combined with dietary supplementation of HMB. In other words, the stimulus to increase muscle mass brought about by weight, or resistance, training is magnified by HMB dietary supplementation.

However, within the context of some applications, it is desirable to increase the aerobic capacity of muscle without a concomitant increase in muscle mass. For example, where the aerobic capacity of cardiac muscle is compromised, it would be desirable to increase the aerobic capacity of the cardiac muscle without a concomitant increase in its muscle mass.

In view of the foregoing, there exists a need for a method by which the aerobic capacity of muscle can be increased without a concomitant increase in muscle mass. The present invention provides such a method as well as a related method thereof. These and other advantages of the present invention, as well as additional inventive features, will be apparent from the description of the invention provided herein.

BRIEF SUMMARY OF THE INVENTION

The present invention provides a method for increasing the aerobic capacity of muscle of an animal, the method comprising administering a dose of HMB to the animal such that the aerobic capacity is increased without a substantial increase in the mass of the muscle. The present invention also provides a method for increasing the amount of hemoglobin in the blood of an animal having muscles, the method comprising administering a dose of HMB to the animal such that the amount of hemoglobin in the animal is increased without a substantial increase in the mass of the muscles.

DESCRIPTION OF THE PREFERRED EMBODIMENTS

The invention may best be understood with reference to the following detailed description of the preferred embodiments. The present invention provides a method for increasing the aerobic capacity of muscle of an animal, the method comprising administering a dose of HMB to the animal such that the aerobic capacity is increased without a substantial increase in the mass of the muscle. The present invention also provides a method for increasing the amount of hemoglobin in the blood of an animal having muscles, the method comprising administering a dose of HMB to the animal such that the amount of hemoglobin in the animal is increased without a substantial increase in the mass of the muscles.

Aerobic Capacity

Aerobic capacity is the maximal rate of oxygen consumption for a given mass of muscle. As used herein, by an increase in the aerobic capacity of muscle it is meant that the aerobic capacity of the muscle is increased without a substantial increase in the mass of the muscle. In other words, the aerobic capacity is increased with respect to a given mass of muscle or with respect to a substantially equivalent mass of muscle.

In one embodiment of the present invention, an increase in the aerobic capacity of muscle of an animal can be effectuated by a method comprising administering a dose of HMB to the animal such that the aerobic capacity is increased. Preferably, the method further comprises a step whereby the animal engages in non-resistance training. While any suitable form of non-resistance training can be used within the context of the present invention, preferred forms of non-resistance training include running, walking, sit-ups, and cycling.

β-hydroxy-β-methylbutyric Acid (HMB)

β-hydroxy-β-methylbutyric acid, or β-hydroxy-isovalaryic acid, can be represented in its free acid form as $(CH_3)_2(OH)CCH_2COOH$. The term "HMB" refers to the compound having the foregoing chemical formula, in both its free acid and salt forms, and derivatives thereof. While any suitable form of HMB which increases the aerobic capacity of muscle can be used within the context of the present invention, preferably, HMB is selected from the group consisting of a free acid, a salt, an ester, and a lactone; more preferably, HMB is a salt. Preferred HMB esters include methyl and ethyl esters, and, preferably, the HMB lactone is an isovalaryl lactone. Both the methyl and ethyl esters of HMB, as well as isovalaryl lactone, and similar lactones, are rapidly converted to HMB in its free acid form.

While any suitable HMB salt can be used within the context of the present invention, preferably, the HMB salt is water-soluble or becomes water-soluble in the stomach or intestines of an animal. More preferably, the HMB salt is selected from the group consisting of a sodium salt, a potassium salt, a magnesium salt, a chromium salt, and a calcium salt. Most preferably, the HMB salt is a calcium salt. However, other non-toxic salts, such as other alkali metal or alkaline earth metal salts, can be used. When HMB is to be administered in an edible form, it is preferred that the salt be dry, non-sticky, and finely-divided for blending with other foodstuffs.

Methods for producing HMB and its derivatives are well known in the art. For example, HMB can be synthesized by oxidation of diacetone alcohol. One suitable procedure is described by Coffman et al., *J. Am. Chem. Soc.,* 80: 2882–2887 (1958). As described therein, β-hydroxy-isovalaryic acid (HMB) is synthesized by an alkaline sodium hypochlorite oxidation of diacetone alcohol. The product is recovered in free acid form, which can be converted to the desired salt. For example, HMB can be prepared as its calcium salt by a procedure similar to that of Coffman et al. in which the free acid of HMB is neutralized with calcium hydroxide and recovered by crystallization from an aqueous ethanol solution. The calcium salt of HMB is commercially available from Metabolic Technologies, Ames, Iowa.

HMB Dose

Any suitable dose of HMB, so as to increase the aerobic capacity of muscle, can be used within the context of the present invention. Methods of calculating proper doses of a drug to achieve a desired effect in animals are well known in the art. The dose of HMB administered to an animal can be stated as a function of the total diet of an animal, where HMB is administered in an edible form, and as a function of the body weight of the animal.

Suitable doses of HMB are described below in terms of a preferred form of HMB for illustration purposes. With respect to administering the calcium salt of HMB in an edible form, such as a foodstuff, the calcium salt of HMB preferably constitutes from about 0.001 wt. % to about 0.5 wt. %, more preferably, from about 0.01 wt. % to about 0.1 wt. %., most preferably, from about 0.02 wt. % to about 0.04 wt. %, of the total diet of the animal.

With respect to the dose of the calcium salt of HMB to administer, as a function of the body weight of the animal, it is preferable to administer at least about 0.05 mg of the calcium salt of HMB per kg of body weight per 24 hours, more preferably, at least about 0.5 mg/kg body weight/24 hours, even more preferably, at least about 15 mg/kg body weight/24 hours, and most preferably, at least about 35 mg/kg body weight/24 hours. Under most circumstances, it will usually not be necessary to administer more than 100 mg/kg body weight/ 24 hours, although higher amounts may be necessary and certainly can be used. Furthermore, the dose of HMB can be administered with any suitable frequency (e.g., one 6 g dose per day or two 3 g doses per day) and over any suitable time period (e.g., a single dose can be administered over a 5 minute time period or over a 1 hour time period).

Of course, when other forms of HMB, e.g., HMB itself, or other salts and/or derivatives of HMB, are used within the context of the present invention, molar equivalents of the foregoing concentrations are preferably used.

Methods of Administering HMB

Methods of administering HMB are well known in the art, and HMB can be administered in any suitable manner. Preferably, HMB is administered either in an edible form or intravenously.

When HMB is administered orally in an edible form, HMB is preferably in the form of a foodstuff or a pharmaceutical composition, more preferably, in the form of a foodstuff. Any suitable foodstuff comprising HMB can be utilized within the context of the present invention. In order to prepare HMB as a foodstuff, HMB will normally be blended with the appropriate foodstuff in such a way that the HMB is substantially uniformly distributed in the foodstuff. Therefore, for example, HMB can be blended with a feed composition or some other foodstuff. Alternatively, HMB can be dissolved in water. Although any suitable pharmaceutical composition comprising HMB can be utilized within the context of the present invention, preferably, HMB is blended with a suitable pharmaceutical carrier, such as dextrose or sucrose, and is subsequently tabulated or encapsulated.

When an HMB salt is orally administered in its edible form to a ruminant, the HMB salt is not subject to significant rumen destruction. Following oral administration, the HMB salt appears to pass intact through the rumen into the intestines of the ruminant where it is absorbed and distributed into the circulatory system.

Furthermore, HMB can be intravenously administered in any suitable manner. For administration via intravenous infusion, HMB is preferably in a water-soluble non-toxic form. Intravenous administration is particularly suitable for hospitalized patients that are undergoing intravenous (IV) therapy. For example, HMB salts can be dissolved in an IV solution (e.g., a saline or glucose solution) being administered to the patient. Also, HMB salts can be added to nutritional IV solutions which may include amino acids and lipids. The amounts of HMB to be administered intravenously can be similar to levels used in oral administration, but it is believed that maximized retention should be obtainable at lesser doses by infusion. Advantages to intravenous infusion over oral administration include the fact that administration via intravenous infusion is more controlled and accurate.

Animal Muscle

While the aerobic capacity of any muscle of any animal, including, but not limited to, humans, can be increased within the context of the present invention, it is preferable that the animal is a mammal. Preferred mammals include humans, small domestic mammals such as cats and dogs, and large domestic mammals such as cattle, sheep, swine, goats, and horses; more preferably, the mammal is a human or a horse, particularly a human. In addition, while the aerobic capacity of any muscle can be increased, preferably, the muscle is that which is substantially required for running, abdominal muscle, skeletal muscle or cardiac muscle.

Method for Increasing Amount of Hemoglobin

An alternative embodiment of the present invention is directed to a method for increasing the amount of hemoglobin in the blood of an animal having muscles, wherein the method comprises administering a dose of HMB to the animal such that the amount of hemoglobin in the animal is increased without a substantial increase in the mass of the muscles. Preferably, the method further comprises engaging the animal in non-resistance training.

As illustrated in the subsequent examples, there exists a relationship between hemoglobin levels in animals and the aerobic capacity of muscles in animals. While not wishing to be bound to any particular theory, it is believed that the increase in the aerobic capacity of muscle is, in part, a product of increased oxygen delivery to muscle which results from increased hemoglobin levels in the blood of the animal.

EXAMPLES

The following examples further illustrate the present invention but, of course, should not be construed as in any way limiting its scope.

Example 1

This example illustrates the stability of HMB in the rumen of ruminants.

Rumen fluid was collected from a fistulated steer. After filtration and dilution (1:4) with an artificial saliva, 25 ml of the solution was added to 50 ml plastic tubes. Each tube was fitted with a one-way valve to allow gases to escape while not allowing air into the tube. Each tube was then gassed with $CO_2$ and incubated at 39° C. After 30 minutes, a solution of KIC or HMB was added to the tube in concentrations to simulate what would be present in the rumen of an animal consuming 0.05 wt. % of the total diet as KIC or HMB. It was estimated that a 50 $\mu M$ concentration would be attained in this case. At timed intervals, 50 $\mu l$ samples of the rumen solution were taken and analyzed for KIC and HMB. The results are shown in Table A.

TABLE A

| Time After Addition (min) | Concentration of KIC ($\mu$M) | Concentration of HMB ($\mu$M) |
|---|---|---|
| 0 | 30* | 60 |
| 15 | 15 | 76 |
| 30 | 4 | 81 |
| 60 | 2 | 71 |
| 240 | 2 | 74 |
| 480 | 1 | 74 |

*The initial concentration of KIC could only be estimated. The initial concentrations should have been approximately 50 $\mu$M, but because of the rapid degradation of KIC in the rumen, KIC was already being degraded before the 0 time collection could be cooled and processed.

The foregoing shows that KIC is rapidly destroyed by the rumen bacteria while HMB is quite stable in a rumen environment.

Example 2

This example illustrates the effect of HMB on horse muscle performance and further illustrates the effect of HMB on hemoglobin levels in the blood of a horse.

Five geldings were given an alfalfa-based supplement containing the calcium salt of HMB, and five geldings were given control supplements containing no HMB. Geldings on the HMB supplement received approximately 1 g of the calcium salt of HMB per 45.5 kg of body weight per day. All horses were exercised 4 times per week on a high-speed treadmill for 12 weeks. The first 6 weeks of non-resistance training was of low to moderate intensity, and the second 6 weeks of non-resistance training was of high intensity. Performance testing was conducted at 0, 6, and 12 weeks and consisted of a 34 minute endurance test interspersed with intense bouts of work. During the 34 minute endurance test, the speed of the treadmill was adjusted so that the geldings had a constant heart rate during the following periods: 10 minutes at a heart rate of 160, 2 minutes at a heart rate of 200, 10 minutes at a heart rate of 160, 2 minutes at a heart rate of 200, and 10 minutes at a heart rate of 160. The following were measured at the 0, 6, and 12 week points: hemoglobin level, red cell level, hematocrit level, blood urea level, blood cholesterol level, and the distance run during the endurance test. The results of the study are summarized in Table B where the percentage change from week 0 is shown.

TABLE B

|  | Control | | HMB | | Average HMB | |
|---|---|---|---|---|---|---|
|  | 6 wks | 12 wks | 6 wks | 12 wks | Change | Signif. |
| Hemoglobin | −7% | −3% | 5% | 10% | 10% | .01 |
| Red Cell | −7% | −4% | 7% | 5% | 9% | .01 |
| Hematocrit | −6% | −3% | 8% | 5% | 10% | .02 |
| Blood Urea | 20% | −4% | 33% | 7% | −25% | .05 |
| Blood Cholesterol | −16% | −16% | 0% | −2% | 15% | .05 |
| Distance Run | −1% | −3% | 5% | 4% | 5% | .25 |

The results illustrate that HMB supplementation increased the aerobic capacity of muscle as indicated by the increased distance that the geldings could run during the 34 minute endurance test while maintaining the same heart rate. Furthermore, HMB supplementation resulted in increased levels of hemoglobin in the geldings.

Example 3

This example illustrates the effect of HMB on abdominal muscle work and also demonstrates the effect of HMB on non-resistive exercise performed to exhaustion.

Twenty-seven college-age males were randomly assigned to one of two treatment groups. The subjects' body weight averaged 82.7±1.6 kg with a range of 64 to 99 kg. One treatment group received 3.0 g of the calcium salt of HMB per day in orange juice, and the other treatment group (i.e., the control group) received no HMB supplementation. The HMB supplementation was divided equally between a morning and evening supplementation such that each subject which received HMB took half of the daily HMB with breakfast and the other half with the evening meal. A total of 5 trunk non-resistance exercise sessions were performed by each subject over a 3 week period of time. Trunk workouts included situps and hyperextensions (i.e., non-resistance training). The exercises were performed by the subjects until the subjects reached exhaustion (i.e., until the subjects could no longer perform any more of the exercises). The results from the 3 week study are summarized in Table C where the number of efforts before exhaustion is shown.

TABLE C

| Group | Start | 3 weeks | Net Change | Net Effect of HMB Signif. |
|---|---|---|---|---|
| Control-Number Situps | 14 | 11.5 | −2.5 | |
| 3 g HMB-Number Situps | 10.5 | 12.5 | 2 | .05 |
| Control-Number of Hyperextensions | 22 | 28 | 6 | |
| 3 g HMB-Number of Hyperextensions | 20 | 39 | 19 | .01 |

The results illustrate that HMB significantly increased the number of exercise replications that the subjects could perform prior to exhaustion, thus indicating an increase in the aerobic capacity of muscles.

Example 4

This example illustrates the effect that HMB has on maximal oxygen consumption ($VO_2$ peak), maximal lactate (LAmax) concentration, and lactate threshold (LT) in endurance trained cyclists.

Eight cyclists, in a double-blind experiment, completed 3 supplementation periods in which the diets of the cyclists were supplemented with HMB. Each period was 2 weeks in duration and was followed by a 2 week washout period in which no HMB supplementation was given. Supplements comprised 3 g of HMB per day, 3 g of leucine per day, and a placebo of 3 g of cornstarch per day. Prior to and following each supplementation period, cyclists completed a graded cycle ergometry test. Each stage of the graded test was 3 minutes in duration. A blood sample was obtained during the last 20 seconds of each stage and immediately following exercise for determination of LAmax. LT was defined as the $VO_2$ that corresponded to 2 mM blood lactate. Table D shows the peak oxygen consumption ($VO_2$peak), the time to reach $VO_2$peak, and blood lactate at $VO_2$peak before and after 2 weeks of either placebo, HMB, or leucine supplementation.

TABLE D

|  | VO$_2$peak (L/min) | Minutes to Reach VO$_2$peak | Lactate at VO$_2$peak (mmol/L) |
|---|---|---|---|
| Control Trial | | | |
| Pre | 4.71 ± 0.16 | 22.4 ± 0.9 | 7.9 ± 1.1 |
| Post | 4.60 ± 0.23 | 21.6 ± 1.4 | 7.5 ± 1.6 |
| % change | −2.6 ± 2.6 | −4.1 ± 3.4 | −8.1 ± 6.7 |
| HMB Trial | | | |
| Pre | 4.60 ± 0.14 | 21.9 ± 0.9 | 7.6 ± 1.1 |
| Post | 4.75 ± 0.15# | 22.7 ± 1.1# | 8.1 ± 1.1 |
| % change | 4.0 ± 1.4* | 3.6 ± 1.5 | 11.1 ± 9.7 |
| Leucine Trial | | | |
| Pre | 4.70 ± 0.17 | 22.2 ± 1.1 | 6.7 ± 0.9 |
| Post | 4.60 ± 0.14 | 21.6 ± 0.9 | 6.8 ± 0.8 |
| % change | −1.9 ± 1.3 | −2.4 ± 2.1 | −0.4 ± 10.9 |

Values are reported as mean ± SE.
*, $P < 0.05$ compared to control and leucine trials.
, $P < 0.05$ compared to pretest.

As the results indicate, two weeks of HMB supplementation resulted in a significant increase in VO$_2$peak and, thus, indicates an increase in the aerobic capacity of muscles. The percent increase in VO$_2$peak was significantly greater with HMB than with either leucine or the placebo control. Furthermore, the lactate threshold of muscles was increased as a result of HMB supplementation.

All of the references cited herein, including patents, patent applications, and publications, are hereby incorporated in their entireties by reference.

While this invention has been described with an emphasis upon preferred embodiments, it will be obvious to those of ordinary skill in the art that variations of the preferred embodiments may be used and that it is intended that the invention may be practiced otherwise than as specifically described herein. Accordingly, this invention includes all modifications encompassed within the spirit and scope of the invention as defined by the following claims.

What is claimed is:

1. A method for increasing the aerobic capacity of muscle of an animal, said method comprising:
   administering β-hydroxy-β-methylbutyric acid (HMB) to said animal in an amount effective to increase said aerobic capacity while the mass of said muscle remains the same or substantially equivalent.

2. The method of claim 1, further comprising the step of engaging said animal in non-resistance training.

3. The method of claim 1, wherein said dose is the molar equivalent of at least 0.05 mg of the calcium salt of HMB per kg of said animal per 24 hours.

4. The method of claim 1, wherein said HMB is selected from the group consisting of its free acid form, its salt, its ester, and its lactone.

5. The method of claim 4, wherein said salt is selected from the group consisting of a sodium salt, a potassium salt, a magnesium salt, a chromium salt, and a calcium salt.

6. The method of claim 5, wherein said salt is a calcium salt.

7. The method of claim 4, wherein said ester is selected from the group consisting of methyl esters and ethyl esters.

8. The method of claim 4, wherein said HMB is an HMB isovalaryl lactone.

9. The method of claim 1, wherein said animal is a mammal.

10. The method of claim 1, wherein said animal is a human or a horse.

11. The method of claim 9, wherein said animal is a human and said muscle is abdominal muscle.

12. The method of claim 1, wherein said HMB is administered to said animal in an edible form.

13. The method of claim 12, wherein said edible form is a foodstuff.

14. A method for increasing the amount of hemoglobin in the blood of an animal having muscles, said method comprising:
   administering HMB to said animal in an amount effective to increase the amount of hemoglobin in said animal while the mass of said muscles remains the same or substantially equivalent.

15. The method of claim 14 further comprising the step of engaging said animal in non-resistance training.

16. The method of claim 14, wherein said animal is a mammal.

17. The method of claim 14, wherein said animal is a human or a horse.

* * * * *